United States Patent [19]
Kohno

[11] Patent Number: 5,448,350
[45] Date of Patent: Sep. 5, 1995

[54] SURFACE STATE INSPECTION APPARATUS AND EXPOSURE APPARATUS INCLUDING THE SAME

[75] Inventor: Michio Kohno, Tokyo, Japan

[73] Assignee: Canon Kabushiki Kaisha, Tokyo, Japan

[21] Appl. No.: 352,444

[22] Filed: Dec. 9, 1994

Related U.S. Application Data

[63] Continuation of Ser. No. 79,844, Jun. 22, 1993, abandoned, which is a continuation of Ser. No. 729,336, Jul. 12, 1991, abandoned.

[30] Foreign Application Priority Data

Jul. 19, 1990 [JP] Japan ................ 2-192271

[51] Int. Cl.$^6$ ............... G01N 21/88; G01N 21/89
[52] U.S. Cl. ................... 356/237; 356/431; 250/559.42; 250/559.48
[58] Field of Search ........... 356/237, 239, 336, 338, 356/340, 342, 445–446, 429–431, 371, 376, 394, 619, 202, 203; 250/234–236, 571–572, 563, 574

[56] References Cited

U.S. PATENT DOCUMENTS

| | | | |
|---|---|---|---|
| 4,097,160 | 6/1978 | Yataki et al. | 356/237 |
| 4,627,734 | 12/1986 | Rioux | 356/376 |
| 4,795,911 | 1/1989 | Kohno et al. | 250/572 |
| 4,831,274 | 5/1989 | Kohno et al. | 250/563 |
| 4,871,257 | 10/1989 | Suzuki et al. | 356/237 |
| 4,965,454 | 10/1990 | Yamauchi et al. | 356/237 |
| 4,999,511 | 3/1991 | Kohno | 250/572 |
| 5,004,929 | 4/1991 | Kakinoki et al. | 356/376 |
| 5,017,798 | 5/1991 | Murakami et al. | 250/572 |
| 5,072,128 | 12/1991 | Hayano et al. | 356/237 |

FOREIGN PATENT DOCUMENTS

| | | | |
|---|---|---|---|
| 0263827 | 1/1989 | Germany | 356/237 |
| 0222756 | 11/1985 | Japan | 356/237 |
| 0046239 | 2/1987 | Japan | 356/237 |

*Primary Examiner*—Hoa Q. Pham
*Attorney, Agent, or Firm*—Fitzpatrick, Cella, Harper & Scinto

[57] ABSTRACT

This invention relates to a surface state inspection apparatus, and more particularly, to a surface state inspection apparatus which is suitable for detecting foreign particles or pattern defects on a pattern or on a surface of a photomask, a reticle or the like, serving as an original plate for pattern transfer in a semiconductor exposure apparatus. Light beams issued from a point to be inspected are guided to an aperture diaphragm using an optical system from a plurality of directions, and further, to a common detector. Hence, the present invention provides the effects that the amount of scattered light detected by the common detector can be greatly increased without providing a large condenser optical system, thereby increasing the S/N ratio, and a foreign particle or a defect at the point to be inspected is completely detected even if the outgoing direction of scattered light from the foreign particle or the defect has a peculiarity.

16 Claims, 7 Drawing Sheets

SURFACE STATE INSPECTION APPARATUS AND EXPOSURE APPARATUS INCLUDING THE SAME

This application is a continuation of prior application, Ser. No. 08/079,844 filed Jun. 22, 1993, which application is a continuation of prior application, Ser. No. 07/729,336 filed Jul. 12, 1991, both now abandoned.

BACKGROUND OF THE INVENTION

1. Field of the Invention

This invention relates to a surface state inspection apparatus, and more particularly, to a surface state inspection apparatus which is suitable for detecting foreign particles or pattern defects on a pattern or on a surface of a photomask, a reticle or the like (hereinafter generically termed a reticle), serving as an original plate for pattern transfer in a semiconductor exposure apparatus.

2. Description of the Prior Art

In general, in integrated circuit (IC) production processes, a circuit pattern for exposure formed on a reticle substrate is transferred onto the surface of a wafer coated with a resist using a semiconductor printing apparatus (a stepper or a mask aligner), to produce ICs.

At that time, if foreign particles, such as dust or the like, are present on the surface of the substrate, the foreign particles are simultaneously transferred, causing a decrease in the yield of the IC production.

Figure 1:
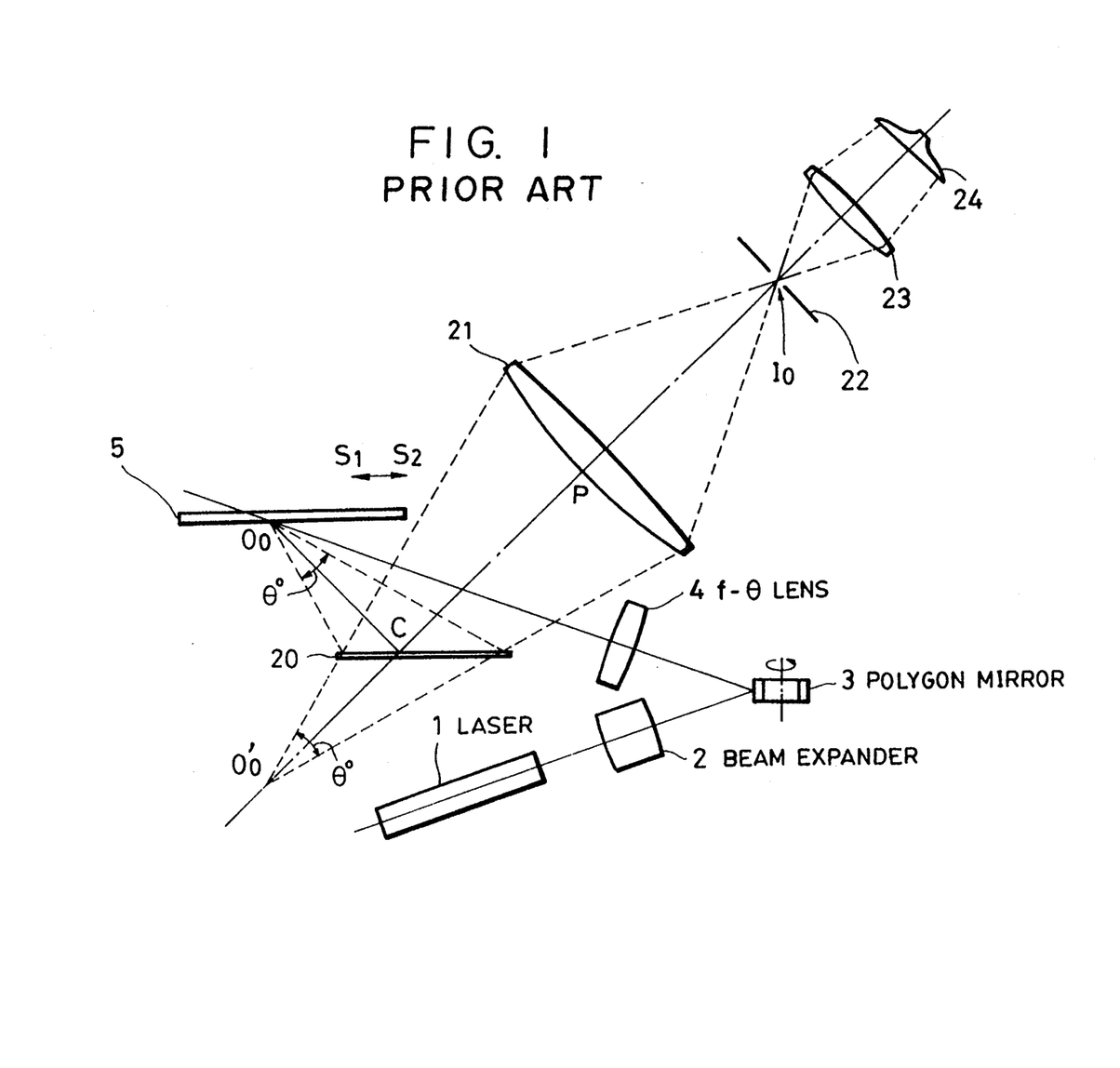
FIG. 1 is a diagram illustrating a conventional apparatus.

Particularly, when a plurality of circuit patterns are printed on a wafer by a step-and-repeat method using a reticle, one foreign particle on the reticle is printed on the entire surface of the wafer, greatly decreasing the yield of the IC production. Accordingly, it is indispensable to detect the presence of foreign particles on a substrate in an IC production process, and various inspection methods have been proposed. FIG. 1 is an example of such a method. In FIG. 1, a laser beam emitted from a laser light source 1 is expanded by a beam expander 2. Subsequently, the laser beam is condensed onto a reticle 5 by an f-$\theta$ lens 4 while the reticle 5 is being scanned by a polygon mirror 3 (or a light scanning element represented by a vibrating mirror). The beam scanning direction is perpendicular to the plane of FIG. 1. By performing stage scanning in the directions shown by double-headed arrows $S_1$ and $S_2$ within the plane of FIG. 1 (the direction orthogonal to the beam scanning direction), the inspection beam is projected (raster scanning) onto the entire surface of the reticle 5.

Figure 2:
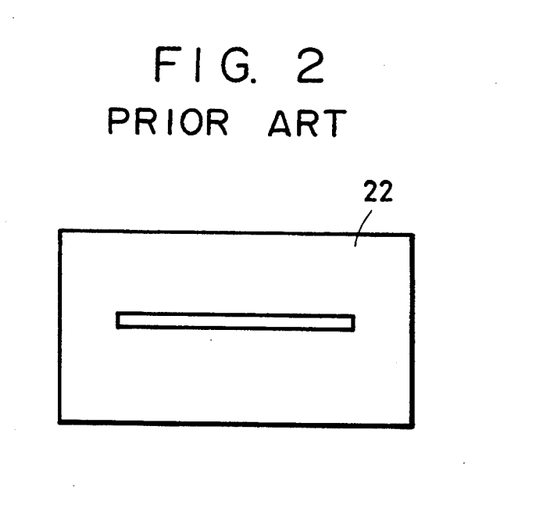
FIG. 2 is a diagram illustrating a field stop used in the conventional apparatus.

If a foreign particle is present on point $O_0$ on the reticle 5 during the beam scanning, a portion of the light diffused by the foreign particle also returns to the incident side (the right side of FIG. 1) of the beam (backscattering light). A mirror 20 is provided for reflecting the scattered light from point $O_0$, and the point $O_0$ is reimaged on a field stop 22 using a condenser lens 21. The field stop 22 is provided in order to cut flare light from portions other than the point $O_0$, and includes a rectangular aperture (the direction of its longer side coincides with the scanning direction of the beam), as shown in FIG. 2. Scattered light beams passing through this aperture diffuse again, but are condensed by a condenser lens 23, and are received by a photomultiplier 24.

The optical relationship among the light-issuing point $O_0$, the condenser lens 21 and the field stop 22 will now be explained. The diffused light beams from the point $O_0$ are reflected by the mirror 20. If a virtual image $O'_0$ of the point $O_0$ produced by the mirror 20 is considered, it can be deemed that the light beam emanating from the point $O'_0$ is imaged on a point $I_0$ on the image surface by the condenser lens 21. The field stop 22 is arranged so that its aperture coincides with the point $I_0$.

In receiving scattered light, it is desirable that a foreign particle which has a peculiarity in the scattering direction can also be detected. The configuration of the conventional apparatus has a disadvantage that, for the above-described purpose, and in order to increase the amount of detected light, if it is intended to receive the scattered light from the point $O_0$ with a wide receiving angle (angle $\theta°$ in FIG. 1), the aperture of the condenser lens 21 must be greatly increased. Particularly in an optical system as shown in FIG. 1 wherein scanning of an object to be inspected is performed, a long operational distance ($O_0-C+C-P$ in FIG. 1) for the scanning must be provided, increasing the aperture of the condenser lens 21. For example, if it is assumed that the operational distance equals 300 mm and the receiving angle for the light beam $\theta°$ equals 30°, the diameter of the condenser lens in the plane of FIG. 1 becomes as large as $$300 \text{ mm} \times \tan(30°/2) \times 2 \fallingdotseq 160 \text{ mm}.$$

A most widely used inspection apparatus of this kind is an apparatus for inspecting foreign particles on a reticle mounted on a semiconductor printing apparatus (stepper). Also, in this apparatus, increasing the amount of scattered light from a foreign particle as much as possible and widening the angle for receiving the light are necessary conditions for increasing the detection rate for foreign particles. On the other hand, making an inspection unit as small as possible is an important factor in order to mount such an apparatus on a stepper. In the conventional apparatus, it has been difficult to satisfy the above-described contradictory requirements. That is, the conventional apparatus has a disadvantage that, if the size of the inspection unit is reduced, the size of the condenser lens 21 is inevitably reduced. The amount of received scattered light from an object to be inspected and the angle for receiving the scattered light are thereby reduced, and hence, sufficient detection capability cannot be obtained.

SUMMARY OF THE INVENTION

The present invention has been made in consideration of the above-described problems.

it is an object of the present invention to provide a surface state inspection apparatus which has an effect of detecting any foreign particles which issue scattered light having a peculiarity in the scattering direction, in a manner equivalent to increasing the receiving angle for scattered light beams from the foreign particle, and which can increase the amount of received light irrespective of a small particle size.

To achieve this object, according to the present invention there is provided an apparatus for inspecting a surface state of a surface being inspected. The apparatus comprises an illuminating system for illuminating a portion of the surface being inspected, a condensing optical system for condensing light from the portion of the surface illuminated by the illuminating system, the condensing optical system comprising an aperture diaphragm, an optical system for guiding light from the portion of the surface illuminated by the illuminating system to the condensing optical system, the optical system being disposed so that at least one of the portion being inspected and a conjugate image thereof is aligned with the aperture diaphragm from a plurality of directions, and a photodetector for receiving light from the surface being illuminated by the illuminating system and passing through the optical system and the condensing optical system from the plurality of directions, the photodetector converting the received light into signals representing a surface state of the portion being inspected.

To achieve the above-noted objects, the present invention also provides an apparatus for performing exposure transfer of a pattern onto a photosensitive member. This apparatus includes an exposure system for performing exposure transfer of the pattern of an original plate onto the photosensitive member, an illuminating system for illuminating a portion being inspected of a surface of the original plate involved in the pattern transfer, as well as the condensing optical system, the optical system and the photodetector of the apparatus discussed above.

To achieve the above-noted objects, the present invention also provides a method of inspecting a surface state of a surface being inspected. The method includes the steps of illuminating a portion of the surface being inspected, condensing light from the illuminated portion of the surface using a condensing optical system, the condensing optical system including an aperture diaphragm, guiding light from the illuminated portion of the surface to the condensing optical system, the guiding being performed so that the light from a portion of the surface is guided to at least one of the aperture diaphragm and a conjugate image thereof from a plurality of directions, receiving, by a photodetector, light from the illuminated surface being inspected, the light passing through an optical system and the condensing system from the plurality of directions and converting the light received by the detector into signals representing a surface state of the portion being inspected.

The foregoing and other objects and features of the present invention will become more apparent from the following detailed description of the preferred embodiments taken in connection with the accompanying drawings.

DETAILED DESCRIPTION OF THE PREFERRED EMBODIMENTS

Figure 3:
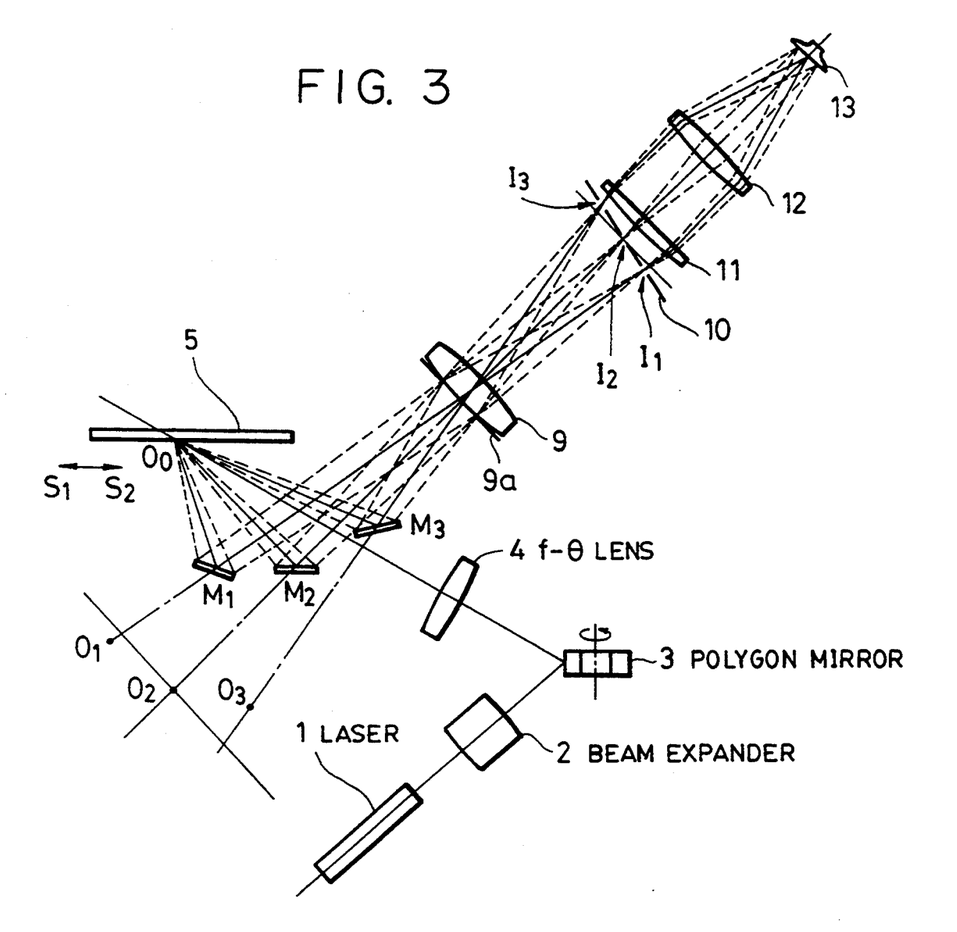
FIG. 3 is a schematic diagram of a surface state inspection apparatus according to a first embodiment of the present invention.

FIG. 3 is a schematic diagram of a surface state inspection apparatus according to a first embodiment of the present invention. Like components as those shown in FIG. 1 are indicated by like reference numerals, A configuration wherein a light beam emitted From a laser light source 1 is projected onto a reticle 5, and is scanned in a direction perpendicular to the plane of FIG. 3 by a polygon mirror 3 and an f-$\theta$ lens 4, a configuration wherein the reticle 5 is moved in a direction (directions represented by double-headed arrows $S_1$ and $S_2$ within the plane of FIG. 3) orthogonal to the direction of beam scanning by a stage (not shown), and scanning of the entire surface to be inspected by the above-described configurations are the same as in the FIG. 1 apparatus. In FIG. 3, mirrors $M_1$, $M_2$ and $M_3$ are disposed so as to view point $O_0$ to be inspected from an aperture diaphragm (to be described later). Each of the mirrors $M_1$, $M_2$ and $M_3$ extends in the direction of beam scanning (a direction perpendicular to the plane of FIG. 3) so as to view from end to end a region of the reticle 5 to be inspected along the direction of beam scanning. A condenser lens 9 includes an aperture diaphragm 9a for forming a pupil in front of the lens 9, and condenses light reflected from the mirrors $M_1$, $M_2$ and $M_3$. A field stop 10 includes apertures at positions nearly conjugate to the point $O_0$ to be inspected with respect to the common condenser lens 9 via the respective mirrors $M_1$, $M_2$ and $M_3$, that is, near positions $I_1$, $I_2$ and $I_3$. Also shown are a field lens 11, a condenser lens 12 and a photomultiplier 13. Light beams passing through the apertures near the positions $I_1$, $I_2$ and $I_3$ are received by the photomultiplier 13 via the field lens 11 and the condenser lens 12.

The mirrors $M_1$, $M_2$ and $M_3$ are disposed at positions where scattered light (backscattering light) beams on the incident side of light beams (the right side in FIG. 3) from a foreign particle or the like are received, other than positions where specular reflection light beams from the surface to be inspected are incident. Light from each mirror is detected through the field stop 10. Accordingly, if the surface to be inspected is a blank surface (a surface where a pattern is not formed) of the reticle 5, the photomultiplier 13 substantially detects only scattered light from a foreign particle or the like on the surface to be inspected. If the surface to be inspected is a pattern (forming) surface, only scattered light from a foreign particle or the like on the surface to be inspected may be substantially detected in the same manner, if the direction of the optical axis of the optical system following the condenser lens 9 coincides with a direction in which diffracted light from the pattern scarcely issues, or if an analyzer for filtering diffracted light from the pattern is inserted within any portion of the optical system in addition to the above-described configuration.

The most important feature of the present invention is that, in order to receive scattered light beams from a foreign particle on the reticle, the plurality of mirrors $M_1$ and $M_3$ eccentrically aligned relative to the optical axis of the condenser lens 9 for receiving light are provided between the lens 9 and the light-issuing point $O_0$ serving as a position to be inspected.

For example, light beams issued from the light-issuing point $O_0$ and reflected by the mirror $M_2$ are imaged on point. $I_2$. In the same manner, light beams issued from the point $O_0$ and reflected by the mirrors $M_1$ and $M_3$ are also imaged at point $I_2$ on or near a plane perpendicular to the optical axis of the lens 9.

In the above-described imaging relationship, the positional relationship among the three mirrors is such that the mirror $M_2$ is disposed on the optical axis of the condenser lens 9, but the lenses $M_1$ and $M_3$ are eccentrically disposed relative to the optical axis. A virtual image $O_2$ of the point $O_0$ produced by the mirror $M_2$ is produced on the optical axis of the condenser lens 9, and the virtual image $O_2$ is imaged on an image point ($I_2$) on the optical axis by the condenser lens 9. On the other hand, virtual images $O_1$ and $O_3$ of the point $O_0$ produced by the mirrors $M_1$ and $M_3$ are produced away from the optical axis by the mirrors $M_1$ and $M_3$, and the virtual images $O_1$ and $O_3$ are imaged on image points ($I_1$ and $I_3$) away from the optical axis by the condenser lens 9. The positions of the virtual images $O_1$ and $O_3$ relative to the optical axis are not necessarily within a plane including the virtual image $O_2$, and are set so as to be perpendicular to the optical axis. As shown in FIG. 3, the virtual images $O_1$ and $O_3$ may deviate from the above-described plane in the direction of the optical axis in accordance with the alignment (positions and angles) of the mirrors $M_1$ and $M_3$. In such a case, the image points ($I_1$ and $I_3$) also deviate relative to the image point $I_2$ in the direction of the optical axis in accordance with the deviation of the virtual images $O_1$ and $O_3$.

The field stop 10 includes apertures for shielding unnecessary flare light and for passing only light beams contributing to imaging of the image points ($I_1$, $I_2$ and $I_3$). The position of the field stop 10 in the direction of the optical axis is shifted in accordance with the positions of the image points $I_1$ and $I_3$. In practice, since the laser beam scans the reticle in a direction orthogonal to the plane of FIG. 3, each of the apertures on the field stop 10 has the shape of a rectangle having its longer side in a direction orthogonal to the plane of FIG. 3.

Figure 4:
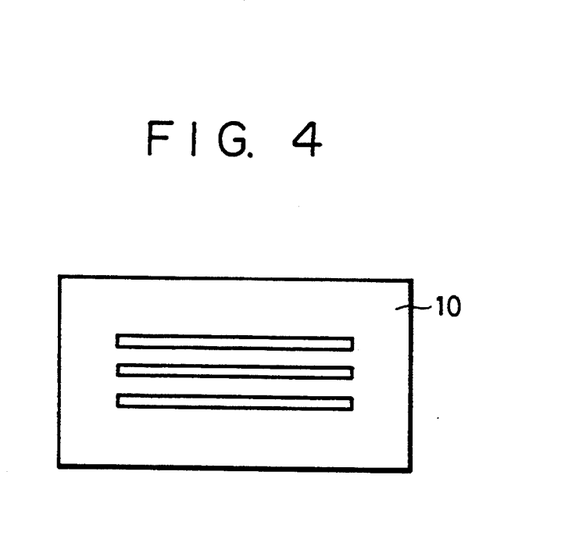
FIG. 4 is a front view of a field stop used in the FIG. 3 apparatus.

FIG. 4 is a front view of the field stop 10.

Light beams passing through the field stop 10 are condensed onto the photomultiplier 13 by the field lens 11 and the condenser lens 12, and are subjected to photoelectric conversion. The obtained signal is transmitted to a signal processing unit (not shown), where the presence of a foreign particle or the like is determined, and the result of the determination is output. Since such signal processing well known, explanation thereof will be omitted.

As described above, in the present embodiment, the mirrors $M_1$, $M_2$ and $M_3$ are provided so as to view the point $O_0$ to be inspected from the aperture diaphragm 9a (an aperture stop image on a plane conjugate to the aperture stop 9a may also be used) from a plurality of directions, and to form different virtual images of the point $O_0$ to be inspected. Light beams from the respective mirrors are condensed on the common condenser lens, and are guided to the single detector. It is thereby possible to guide light beams to the single aperture diaphragm (or an image of the aperture diaphragm) from the plurality of directions, and to greatly increase the amount of detected scattered light beams by the single detector. As a result, the S/N ratio can be increased. The present embodiment also has the effect of completely detecting a foreign particle or a defect at a point to be inspected even if the outgoing/direction of scattered light beams emanating from the foreign particle or the defect has a peculiarity, since the present embodiment has a configuration such that light beams having outgoing angles greatly different from one another can be nearly equally detected. Furthermore, since a portion of any wide light beams issued from a point to be inspected is guided to the detector by dividing that portion into light beams issued from a plurality of objects, it is possible to provide a compact condensing optical system providing the capability of nearly equally detecting light beams having outgoing angles greatly different from one another. Moreover, since the optical lengths of light beams incident upon the common condenser lens via the respective mirrors are adjusted so that outgoing light beams from the respective mirrors form images of a point to be inspected at positions approximately on the same plane by the condenser lens 9, it is possible to easily remove unnecessary scattered light beams in the respective light beams by a simple field stop which merely includes the apertures at positions corresponding to respective image positions on a single substrate.

In the present embodiment, the photomultiplier 13 is disposed at a position conjugate to the aperture diaphragm 9a. It is thereby possible to minimize variations in the distribution of illuminance produced on the photomultiplier 13 due to any change in the point to be inspected in accordance with the light beam scanning. That is, it is possible to almost uniformly receive light beams from any point on the surface to be inspected. Moreover, the result of detection is not influenced by any unevenness in sensitivity on the surface to be detected.

In the above-described embodiment, the same effect of the present invention may be provided even if the mirrors $M_1$, $M_2$ and $M_3$ are not plane mirrors, but are portions of a concave mirror.

Figure 5:
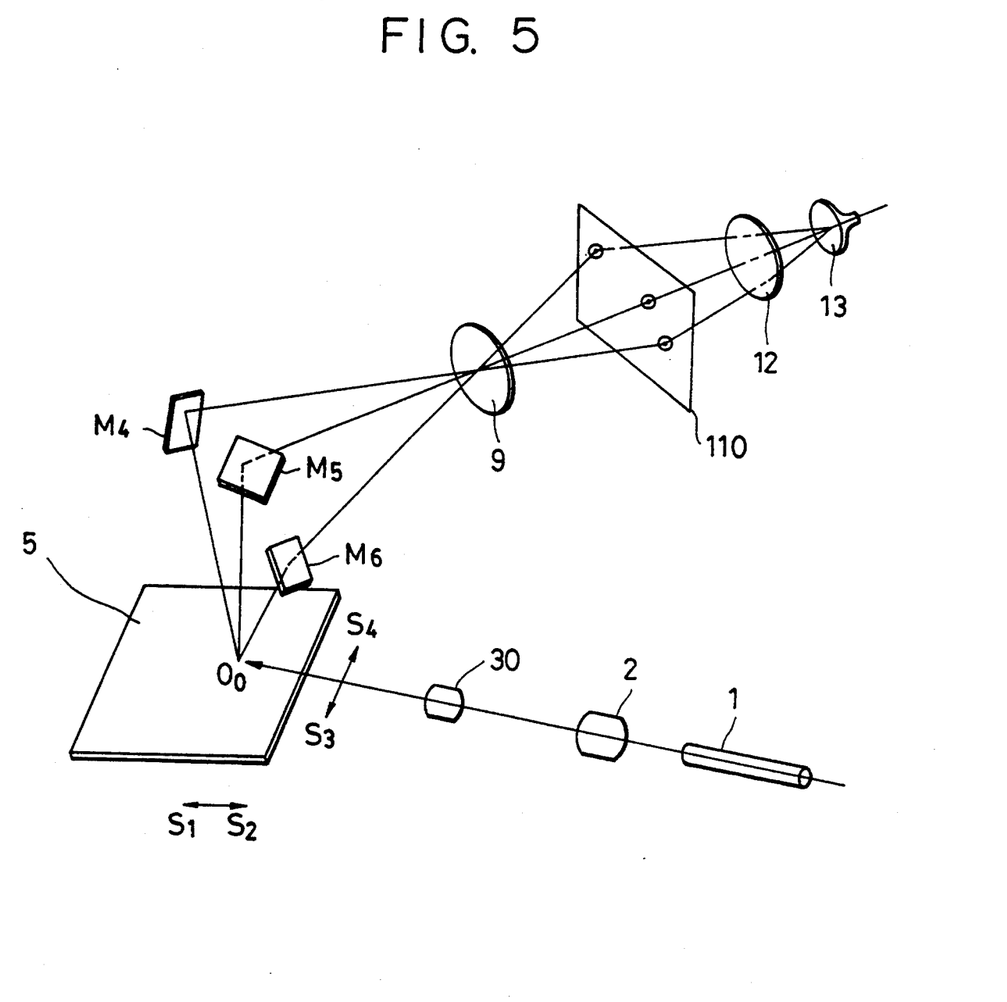
FIG. 5 is a schematic diagram of a surface state inspection apparatus according to a second embodiment of the present invention.

FIG. 5 is a schematic diagram of a surface state inspection apparatus according to a second embodiment of the present invention.

In the FIG. 3 embodiment, in order to inspect the entire surface of the reticle, two-dimensional scanning utilizing laser scanning in one direction and stage movement in a direction crossing that direction is performed. In addition, the direction to eccentrically dispose the mirrors ($M_1$, $M_2$ and $M_3$) is limited to a cross section (within the plane of FIG. 3) orthogonal to the laser scanning direction. To the contrary, in the present embodiment, only stage movement is utilized for two-dimensional scanning in two directions. That is, by moving a stage in two directions, i.e., in the directions indicated by double-headed arrows $S_1$ and $S_2$ and $S_3$ and $S_4$ in FIG. 5, while fixing the laser beam, the entire region to be inspected on the reticle is sequentially subjected to two-dimensional scanning.

The beam incident optical system shown in FIG. 5 differs from the system shown in FIG. 3 in that no polygon mirror is present and the f-$\theta$ lens 4 is replaced with an object lens 30, serving as a typical condenser lens. A laser light source 1 and a beam expander 2 have the same functions as those shown in FIG. 3. Unlike the mirrors $M_1$, $M_2$ and $M_3$ shown in FIG. 3, mirrors $M_4$, $M_5$ and $M_6$ are eccentrically disposed within a two-dimensional space. Virtual images of point $O_0$ to be inspected formed by the respective mirrors are imaged approximately on the same plane by a lens 9. A field stop 110 is disposed on or near this plane. In the present embodiment, apertures on the field stop 110 may be pinholes whose number corresponds to the number of mirrors. Light beams passing through the field stop 110 are condensed onto a photomultiplier 13 by a condenser lens 12 as in the FIG. 3 embodiment. An aperture diaphragm 9a (not shown in FIG. 5) is present immediately before the lens 9, as in the FIG. 3 embodiment.

Figure 6:
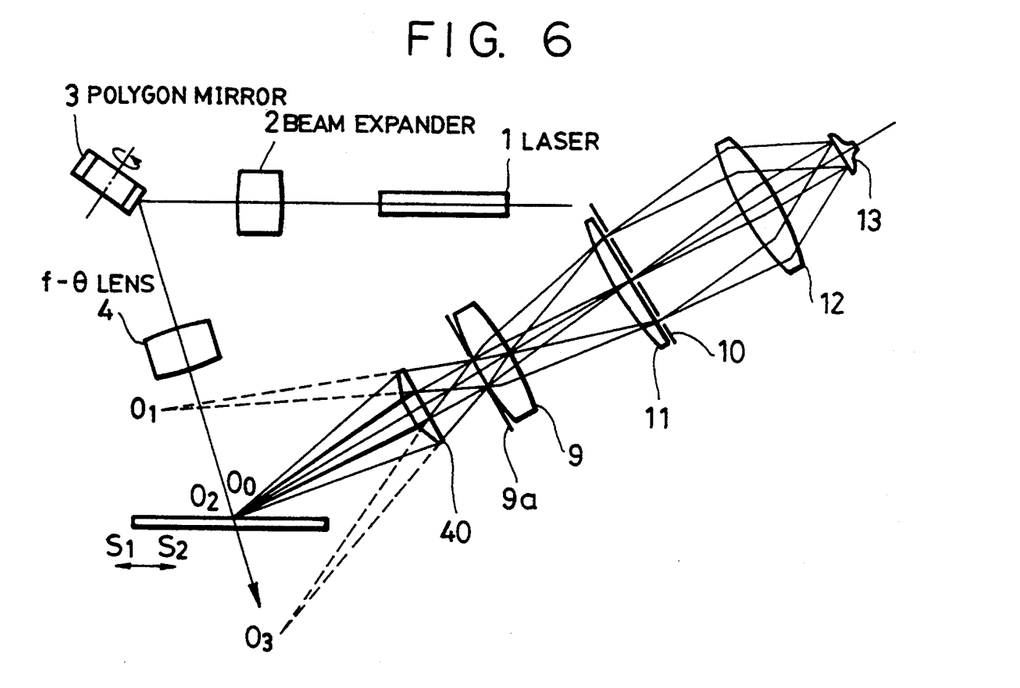
FIG. 6 is a schematic diagram of a surface state inspection apparatus according to a third embodiment of the present invention.

FIG. 6 is a schematic diagram of a surface state inspection apparatus according to a third embodiment of the present invention. In FIG. 6, like components as those shown in FIG. 3 are indicated by like numerals.

Figure 7:
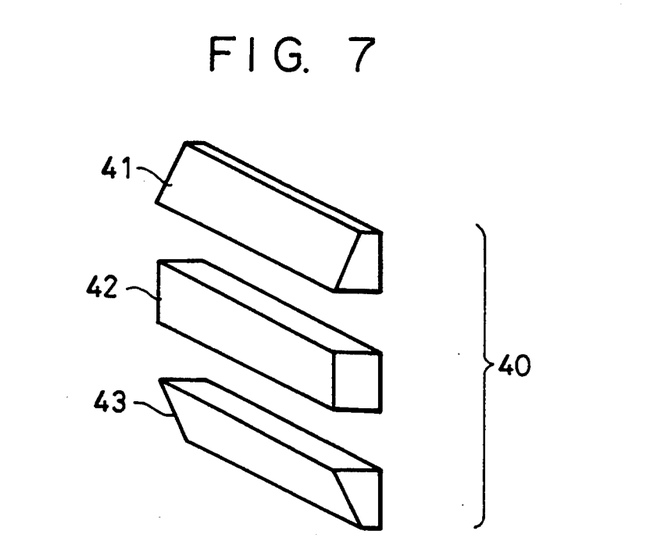
FIG. 7 is a diagram illustrating prisms used in the FIG. 6 apparatus.

The present embodiment differs from the first embodiment in that a composite prism 40 is used in place of the mirrors $M_1$, $M_2$ and $M_3$. As shown in FIG. 7, the composite prism 40 comprises a plurality of (three, in the FIG. 7 embodiment) prisms 41, 42 and 43 each having the longitudinal direction of its slanting face in the scanning direction (a direction perpendicular to the plane of FIG. 6) of the inspection beam. By the function of the composite prism 40, divided images of the point $O_0$ to be inspected are formed at points $O_1$, $O_2$ and $O_3$. Light incident upon each prism of the composite prism 40 issues directly or with refraction in the direction of an aperture of the aperture diaphragm 9a, serving as a pupil, provided before the condenser lens 9 by the function of the prism.

The process of scattered light beams reaching the condenser lens 9, the field stop 10, the condenser lens 12 and the photomultiplier 13 is the same as in the FIG. 3 embodiment. In the present embodiment, however, the field lens 11 is provided before the field stop 10.

The apex angle of each of the prisms 41, 42 and 43 is determined according to the placement of the prism in the optical path, that is, the position and inclination of the prism. The prisms 41, 42 and 43 may be greatly separated from one another in order to provide viewing angles greatly different from one another. FIG. 6 depicts a case wherein the beam is scanned using a polygon mirror. However, as shown in FIG. 5, two-dimensional scanning may be executed by performing two-dimensional stage movement while fixing the beam.

Figure 8A:
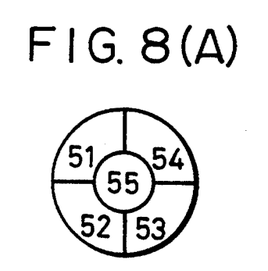
FIGS. 8(A)-8(E) illustrate modified examples of the prisms used in the FIG. 6 apparatus.
Figure 8B:
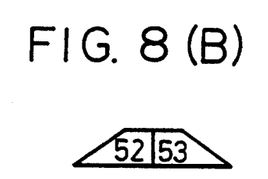
Figure 8C:
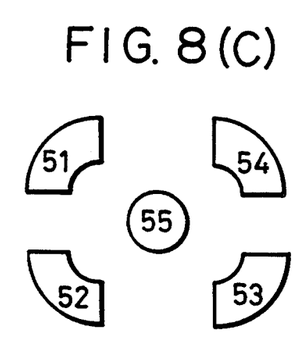
Figure 8D:
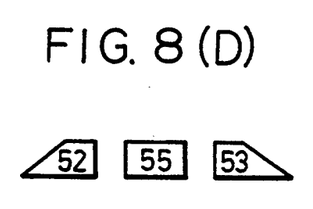
Figure 8E:
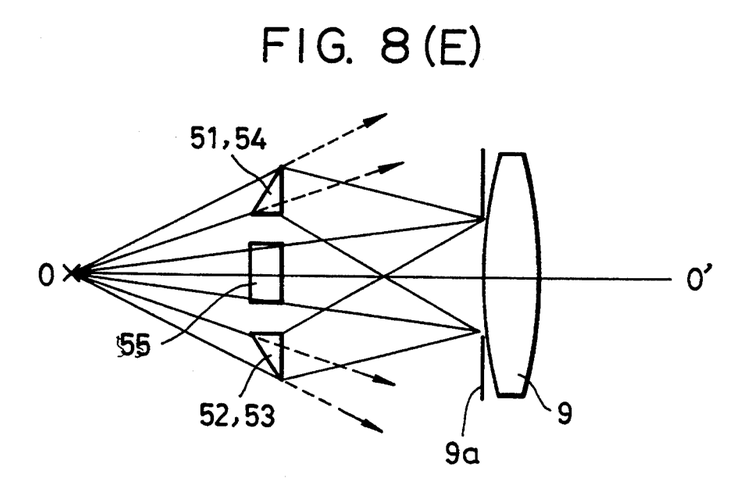

Examples of such operation will now be explained. As shown in FIGS. 8(A)–8(E), a group of prisms (51, 52, 53, 54 and 55) obtained by dividing an optical member having the shape of a circular truncated cone are used in place of the composite prism 40. FIG. 8(A) is a plan view of the optical member before being divided. FIG. 8(B) is a side view of the optical member. FIG. 8(C) illustrates plan views of respective prisms after dividing the optical member into five pieces. FIG. 8(D) is a side view of the divided prisms of FIG. 8(C). FIG. 8(E) illustrates the function of the prisms. It can be considered that, among light beams issued from the light-issuing point O, light beams issued in the direction of the optical axis (OO') of the light-receiving system are issued rotation-symmetrically with respect to this optical axis. FIG. 8(E) is a cross-section of such light beams. Among such light beams, light beams incident upon the prism 55 advance without changing course, because the prism 55 constitutes a parallel plane, and pass through the aperture diaphragm 9a and the condenser lens 9. On the other hand, light beams incident upon the prisms 51–54 are deflected in the direction of the optical axis OO' by the refracting functions of these prisms, and pass through the aperture diaphragm 9a and the condenser lens 9. In this case, pinhole-like openings as shown in FIG. 5 are provided in the field stop 10.(not shown in FIG. 8(E)).

Figure 9:
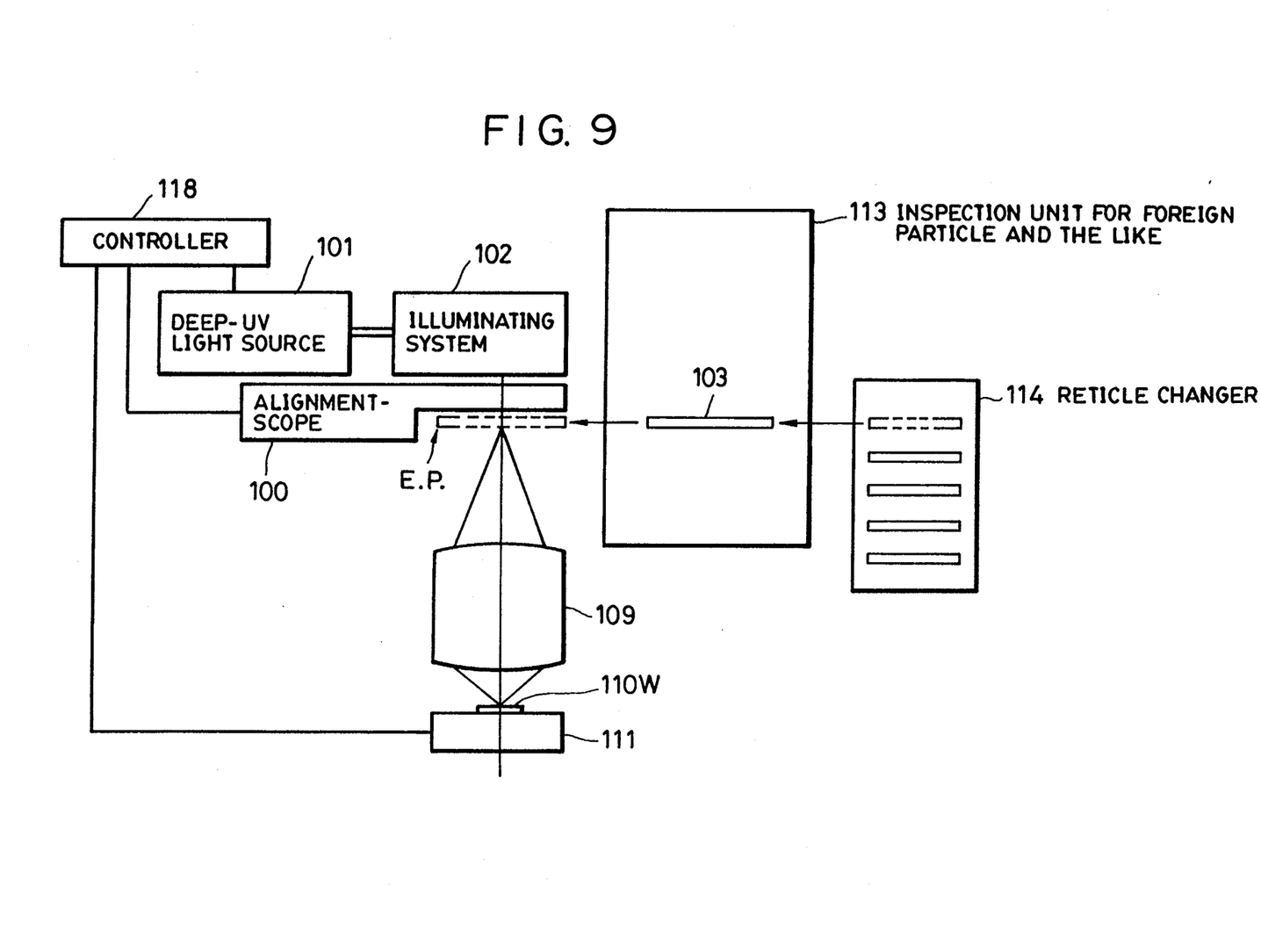
FIG. 9 is a diagram showing the configuration of a semiconductor pointing apparatus including a surface state inspection apparatus according to another embodiment of the present invention.

FIG. 9 is a diagram showing the configuration of a surface state inspection apparatus according to another embodiment of the present invention. In the present embodiment, the entire inspection apparatus is incorporated within a semiconductor printing apparatus.

In FIG. 9, there is shown a deep-UV light source 101, such as an excimer laser or the like. An illuminating system 102 uniformly and simultaneously (at the same time) illuminates the entire region to be inspected of a reticle 103 from above with a predetermined NA (numerical aperture).

An ultra-high-resolution lens system (or mirror system) 109 is used for transferring a reticle pattern onto a wafer 110. In printing, the wafer 110W is exposed while being shifted every one shot in accordance with the stepping movement of a moving stage 111. An alignment optical system 100 is used for aligning the reticle with the wafer before exposure, and includes at least one microscope system for observing the reticle.

A reticle changer 114 is a unit for receiving a plurality of reticles in a standby state. An inspection unit 113 for foreign particles and the like includes all the components shown in FIG. 3, 5 or 6. The inspection unit 113 inspects foreign particles on a reticle before the reticle, which is drawn out from the reticle changer 114, is set in at exposure position (E.P. In FIG. 9).

A controller 118 controls the sequence of alignment, exposure and step movement of the wafer, which are the basic operations of the stepper.

In the above-described configuration, since the principle and operation of the inspection of foreign particles and the like by the unit 113 are the same as in any of the above-described embodiments, explanation thereof will be omitted.

In the above-described respective embodiments, one optical element within the optical system may also have the function of an aperture diaphragm, and an aperture diaphragm may not be separately provided. In such a case, the one optical element will be termed an aperture diaphragm.

As described above, in the foregoing respective embodiments, light beams issued from a point to be inspected are guided to the aperture diaphragm or an image thereof using the optical system from a plurality of directions, and further, to the common detector. Hence, the present invention provides the effects that the amount of scattered light detected by the common detector can be greatly increased without providing a large condensing optical system, thereby increasing the S/N ratio, and a foreign particle or a defect at the point to be inspected is completely detected even if the outgoing direction of scattered light from the foreign particle or the defect has a peculiarity.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An apparatus for inspecting a surface state of a surface being inspected, said apparatus comprising:
   an illuminating system for illuminating a portion of the surface being inspected;
   a condensing optical system for condensing light from the portion of the surface illuminated by said illuminating system, said condensing optical system comprising an aperture diaphragm and a field stop having a plurality of openings;

an optical system for guiding light from the portion of the surface illuminated by said illuminating system to said condensing optical system, said optical system being disposed so that at least one of the portion being inspected and the conjugate image thereof is aligned with said aperture diaphragm from a plurality of directions and so that the light guided through said aperture diaphragm from each of the respective directions passes through a corresponding field stop opening; and a photodetector for receiving light from the surface being inspected illuminated by said illuminating system and passing through said optical system and said condensing system from the plurality of directions, said photodetector converting the received light into signals representing a surface state of the portion being inspected, wherein the plurality of field stop openings are disposed near positions where respective images of the portion of the surface being inspected are formed by light coming from the plurality of directions, and wherein said photodetector detects light transmitted through said field stop.

2. An apparatus according to claim 1, wherein said illuminating system comprises a light source for emitting illuminating light, a scanning optical system for scanning the surface being inspected with the light emitted from said light source in a first direction on the surface being inspected, wherein said apparatus further comprises a stage for moving the surface being inspected in a second direction at an angle to the first direction, such that the entire surface being inspected is subjected to optical scanning by the light scanning of said scanning optical system and movement by said stage.

3. An apparatus according to claim 2, wherein said field stop includes rectangular apertures longitudinal directions of which are disposed in a direction corresponding to the first direction.

4. An apparatus according to claim 1, wherein said optical system comprises a plurality of mirrors arranged such that the portion being inspected can be inspected from each of the plurality of directions.

5. An apparatus according to claim 1, wherein said optical system comprises a plurality of prisms arranged such that the portion being inspected can be inspected from each of the plurality of directions.

6. An apparatus for performing exposure transfer of a pattern onto a photosensitive member, said apparatus comprising:

an exposure system for performing exposure transfer of the pattern of an original plate onto the photosensitive member;

an illuminating system for illuminating a portion being inspected of a surface of the original plate involved in the pattern transfer;

a condensing optical system for condensing light from the portion of the surface illuminated by said illuminating system, said condensing optical system comprising an aperture diaphragm and a field stop having a plurality of openings;

an optical system for guiding light from the portion of the surface illuminated by said illuminating system to said condensing optical system, said optical system being disposed so that at least one of the portion being inspected and the conjugate image thereof is aligned with said aperture diaphragm from a plurality of directions and so that the light guided through said aperture diaphragm from each of the respective directions passes through a corresponding field stop opening; and a photodetector for receiving light from the surface being inspected illuminated by said illuminating system and passing through said optical system and said condensing optical system from the plurality of directions, said photodetector converting the received light into signals representing a surface state of the portion being inspected, wherein the plurality of field stop openings are disposed near positions where respective images of the portion of the surface being inspected are formed by light coming from the plurality of directions, and wherein said photodetector detects light transmitted through said field stop.

7. An apparatus according to claim 6, wherein said illuminating system illuminates a substrate involved in the pattern transfer as the portion being inspected of the surface of the original plate involved in the pattern transfer.

8. A method of inspecting a surface state of a surface being inspected, said method comprising the steps of:

illuminating a portion of the surface being inspected;

condensing light from the illuminated portion of the surface using a condensing optical system, the condensing optical system including an aperture diaphragm and a field stop having a plurality of openings;

guiding light from the illuminated portion of the surface to the condensing optical system, said guiding being performed so that the light from the portion of the surface is guided to at least one of the aperture diaphragm and the conjugate image thereof from a plurality of directions and so that the light guided through the aperture diaphragm from each of the respective directions passes through a corresponding field stop opening;

receiving, by a photodetector, light from the illuminated surface being inspected, the light passing through an optical system and the condensing optical system from the plurality of directions, wherein the plurality of field stop openings are disposed near positions where respective images of the portion of the surface being inspected are formed by light coming from the plurality of directions, and the photodetector detects light transmitted through the field stop; and converting the light received by the photodetector into signals representing a surface state of the portion being inspected.

9. An apparatus for inspecting a surface state of a surface being inspected, said apparatus comprising:

an illuminating system for illuminating a portion of the surface being inspected;

a condensing optical system, having a lens, for collectively condensing light from a plurality of directions from the portion of the surface illuminated by said illuminating system;

an optical system for guiding light from the portion of the surface illuminated by said illuminating system to said condensing optical system, said optical system being arranged to form a plurality of virtual images of the illuminated portion of the surface and being arranged so that light guided to said condensing optical system from the plurality of directions, which respectively correspond to the plurality of virtual images, passes through said lens of said condensing optical system; and a photodetector for receiving light from the surface being inspected illuminated by said illuminating system and passing through said optical system and said lens of said condensing optical system, said photodetector converting the received light into signals representing a surface state of the portion being inspected.

10. An apparatus for performing exposure transfer of a pattern onto a photosensitive member, said apparatus comprising:

an exposure system for performing exposure transfer of the pattern of an original plate onto the photosensitive member;

an illuminating system for illuminating a portion being inspected of a surface of the original plate involved in the pattern transfer;

a condensing optical system, having a lens, for collectively condensing light from a plurality of directions from the portion of the surface illuminated by said illuminating system;

an optical system for guiding light from the portion of the surface illuminated by said illuminating system to said condensing optical system, said optical system being arranged to form a plurality of virtual images of the illuminated portion of the surface and being arranged so that light guided to said condensing optical system from the plurality of directions, which respectively correspond to the plurality of virtual images, passes through said lens of said condensing optical system; and a photodetector for receiving light from the surface being inspected illuminated by said illuminating system and passing through said optical system and said lens of said condensing optical system, said photodetector converting the received light into signals representing a surface state of the portion being inspected.

11. A method of inspecting a surface state of a surface being inspected, said method comprising the steps of:

illuminating a portion of the surface being inspected;

collectively condensing light from a plurality of directions from the illuminated portion of the surface using a condensing optical system having a lens;

guiding light from the illuminated portion of the surface, from the plurality of directions corresponding to a plurality of virtual images of the portion of the surface, so that the light passes through the lens of the condensing optical system;

receiving, by a photodetector, light from the illuminated surface being inspected, the light passing through an optical system and the lens of the condensing optical system from the plurality of directions; and converting the light received by the photodetector into signals representing a surface state of the portion being inspected.

12. A method of producing a device using an apparatus for inspecting a surface state of a surface being inspected, said method comprising:

illuminating a portion of the surface being inspected using an illuminating system;

collectively condensing light, using a condensing optical system having a lens, from a plurality of directions from the portion of the surface illuminated by the illuminating system;

guiding light from the portion of the surface illuminated by the illuminating system to the condensing optical system, using an optical system which is arranged to form a plurality of virtual images of the illuminated portion of the surface, so that the light passes through the lens of the condensing optical system;

receiving, by a photodetector, light from the surface being inspected illuminated by the illuminating system and passing through the optical system and the lens of the condensing optical system; and converting the received light into signals representing a surface state of the portion being inspected.

13. A method of producing a device using an apparatus for performing exposure transfer of a pattern onto a photosensitive member, said method comprising:

performing exposure transfer of the pattern of an original plate onto the photosensitive member;

illuminating, by an illuminating system, a portion being inspected of a surface of the original plate involved in the pattern transfer;

collectively condensing, by a condensing optical system having a lens, light from a plurality of directions from the portion of the surface illuminated by the illuminating system;

guiding light from the portion of the surface illuminated by the illuminating system to the condensing optical system using an optical system, which is arranged to form a plurality of virtual images of the portion of the surface, so that the light passes through the lens of the condensing optical system;

receiving, by a photodetector, light from the surface being inspected illuminated by the illuminating system and passing through the optical system and the lens of the condensing optical system; and converting the received light into signals representing a surface state of the portion being inspected.

14. A method of producing a device by inspecting a surface state of a surface being inspected, said method comprising the steps of:

illuminating a portion of the surface being inspected;

collectively condensing light from a plurality of directions from the illuminated portion of the surface using a condensing optical system having a lens;

guiding light from the illuminated portion of the surface, from the plurality of directions corresponding to a plurality of virtual images of the portion of the surface, to the condensing optical system, so that the light passes through the lens of the condensing optical system;

receiving, by a photodetector, light from the illuminated surface being inspected, the light passing through an optical system and the lens of the condensing optical system from the plurality of directions; and converting the light received by the photodetector into signals representing a surface state of the portion being inspected.

15. An apparatus for inspecting a surface state of a surface being inspected, said apparatus comprising:

an illuminating system for illuminating a portion of the surface being inspected;

a condensing optical system, having a lens, for collectively condensing light from a plurality of directions from the portion of the surface illuminated by said illuminating system;

an optical system for guiding light from the portion of the surface illuminated by said illuminating system, from the plurality of directions corresponding to a plurality of virtual images of the illuminated portion of the surface, to said condensing optical system, said optical system being arranged so that the light guided to said condensing optical system from the plurality of directions passes through said lens of said condensing optical system; and a photodetector for receiving light from the surface being inspected illuminated by said illuminating system and passing through said optical system and said lens of said condensing optical system, said photodetector converting the received light into signals representing a surface state of the portion being inspected.

16. An apparatus for performing exposure transfer of a pattern onto a photosensitive member, said apparatus comprising:

an exposure system for performing exposure transfer of the pattern of an original plate onto the photosensitive member;

an illuminating system for illuminating a portion being inspected of a surface of the original plate involved in the pattern transfer;

a condensing optical system, having a lens, for collectively condensing light from the portion of the surface illuminated by said illuminating system;

an optical system for guiding light from the portion of the surface illuminated by said illuminating system, from the plurality of directions corresponding to a plurality of virtual images of the illuminated portion of the surface, to said condensing optical system, said optical system being arranged so that the light guided to said condensing optical system from the plurality of directions passes through said lens of said condensing optical system; and a photodetector for receiving light from the surface being inspected illuminated by said illuminating system and passing through said optical system and said lens of said condensing optical system, said photodetector converting the received light into signals representing a surface state of the portion being inspected.

* * * * *

UNITED STATES PATENT AND TRADEMARK OFFICE
CERTIFICATE OF CORRECTION

PATENT NO. : 5,448,350
DATED : September 5, 1995
INVENTOR(S) : Michio Kohno

It is certified that error appears in the above-indentified patent and that said Letters Patent is hereby corrected as shown below:

COLUMN 2:

Line 50, "it" should read --It--.

COLUMN 3:

Line 5, ".illuminating" should read --illuminating.--.

COLUMN 4:

Line 9, "numerals," should read --numerals.--; and
Line 10, "From" should read --from--.

UNITED STATES PATENT AND TRADEMARK OFFICE
CERTIFICATE OF CORRECTION

PATENT NO. : 5,448,350
DATED : September 5, 1995
INVENTOR(S) : Michio Yohno

It is certified that error appears in the above-indentified patent and that said Letters Patent is hereby corrected as shown below:

COLUMN 5:

Line 49, "processing" should read --processing is--; and
Line 67, "outgoing/direction" should read --outgoing direction--.

COLUMN 7:

Line 65, "stop 10." should read --stop 10--.

Signed and Sealed this

Thirteenth Day of February, 1996

Attest:

BRUCE LEHMAN

*Attesting Officer*   *Commissioner of Patents and Trademarks*